United States Patent
Liu et al.

(10) Patent No.: US 11,649,489 B2
(45) Date of Patent: May 16, 2023

(54) NUCLEIC ACID SEQUENCING METHOD AND NUCLEIC ACID SEQUENCING KIT

(71) Applicant: BGI SHENZHEN, Shenzhen (CN)

(72) Inventors: Erkai Liu, Shenzhen (CN); Wenwei Zhang, Shenzhen (CN); Ao Chen, Shenzhen (CN); Chongjun Xu, Shenzhen (CN)

(73) Assignee: BGI SHENZHEN, Guangdong (CN)

( * ) Notice: Subject to any disclaimer, the term of this patent is extended or adjusted under 35 U.S.C. 154(b) by 364 days.

(21) Appl. No.: 16/757,719

(22) PCT Filed: Oct. 12, 2018

(86) PCT No.: PCT/CN2018/109992
§ 371 (c)(1),
(2) Date: Apr. 20, 2020

(87) PCT Pub. No.: WO2019/080725
PCT Pub. Date: May 2, 2019

(65) Prior Publication Data
US 2021/0363576 A1  Nov. 25, 2021

(30) Foreign Application Priority Data

Oct. 25, 2017 (CN) .......................... 201711007781.7

(51) Int. Cl.
*C12Q 1/68* (2018.01)
*C12Q 1/6869* (2018.01)
*C12Q 1/6876* (2018.01)

(52) U.S. Cl.
CPC ......... *C12Q 1/6869* (2013.01); *C12Q 1/6876* (2013.01)

(58) Field of Classification Search
CPC ............................ C12Q 1/6869; C12Q 1/6876
See application file for complete search history.

(56) References Cited

U.S. PATENT DOCUMENTS

| | | | |
|---|---|---|---|
| 2003/0207295 A1* | 11/2003 | Gunderson | .......... C12Q 1/6874 435/6.12 |
| 2008/0242560 A1 | 10/2008 | Gunderson et al. | |
| 2009/0170724 A1 | 7/2009 | Balasubramanian et al. | |
| 2011/0039259 A1* | 2/2011 | Ju | .......... C12Q 1/6876 435/6.12 |
| 2011/0076679 A1 | 3/2011 | Shin et al. | |
| 2014/0113282 A1 | 4/2014 | Balasubramanian et al. | |

FOREIGN PATENT DOCUMENTS

| | | |
|---|---|---|
| CN | 101633961 A | 1/2010 |
| CN | 101910410 A | 12/2010 |
| CN | 102030792 A | 4/2011 |
| CN | 104520443 A | 4/2015 |
| CN | 105722850 A | 6/2016 |
| CN | 108165618 A | 6/2018 |
| WO | WO 2009/055617 A1 | 4/2009 |
| WO | WO 2013/188471 A2 | 12/2013 |
| WO | WO 2015/026845 A2 | 2/2015 |

OTHER PUBLICATIONS

Ansorge, "Next-generation DNA sequencing techniques", New Biotechnology, 2009, 25(4): 195-203.
Jiang et al., "Cleavable Linkers in DNA Sequencing by Synthesis", Progress in Chemistry, 2016, 28(1): 58-66, (With only abstract in English).
Liu et al., "Chlamydia pneumoniae AP endonuclease IV could cleave AP sites of double- and single-stranded DNA", Biochimica et Biophysica Acta, 2005, 1753: 217-225.
Mardis, "The impact of next-generation sequencing technology on genetics", Trends in Genetics, 2008, 24(3): 133-141.
Seo et al., "Four-color DNA sequencing by synthesis on a chip using photocleavable fluorescent nucleotides", PNAS, 2005, 102(17): 5926-5931.
Wan et al., "Evaluation of a New HPV Genotyping Assay Base on Semiconductor Sequencing Method", Chin. J. Fam. Plann., 2015, 23(9): 615-619, (With only abstract in English).

* cited by examiner

*Primary Examiner* — Jezia Riley
(74) *Attorney, Agent, or Firm* — James S. Keddie; Bozicevic, Field & Francis LLP

(57) ABSTRACT

Provided are a nucleic acid sequencing method and a nucleic acid sequencing kit. The kit comprises a nucleic acid probe, a ligase, dNTP having a blocking group attached to a 3' end, a polymerase, a reagent 1 for excising the blocking group attached to the 3' end of the dNTP, and a reagent 2 for excising the remaining nucleotides on the nucleic acid probe that are not bound to a to-be-tested base group.

29 Claims, 4 Drawing Sheets

NUCLEIC ACID SEQUENCING METHOD AND NUCLEIC ACID SEQUENCING KIT

CROSS-REFERENCE TO RELATED APPLICATIONS

This application is a § 371 national phase of International Application No. PCT/CN2018/109992, filed on Oct. 12, 2018, which claims the benefit of Chinese Application No. 201711007781.7, filed on Oct. 25, 2017, which applications are incorporated by reference herein.

TECHNICAL FIELD

The present invention belongs to the field of gene sequencing, and relates to a nucleic acid sequencing method and a nucleic acid sequencing kit. In particular, the nucleic acid sequencing method is a DNA sequencing method. In particular, the nucleic acid sequencing kit is a DNA sequencing kit.

BACKGROUND ART

The method of sequencing-by-ligation was developed by Complete Genomics and ABI, respectively, and presented in different forms. The basic principle thereof is that a fluorescently modified DNA probe is ligated by a ligase. The DNA probe is a specific base at certain position to identify the sequence to be tested, and the remaining positions are random sequences to form a complementary strand with another position to be tested. After the ligation reaction, the probe that is not ligated is removed, and then the signal of the ligated probe is detected by an optical means to determine the sequence at that position.

Complete Genomics uses probes that mark four different bases with different fluorophores. There are 4 different bases at the first position of the 5'-terminal of the first group of probes, and the subsequent bases are a random sequence so as to bind to a random sequence to be tested. After being ligated to a primer sequence by a ligase, a fluorescence is detected to obtain the base information at that position. After removing the added sequence, and adding a new sequencing primer, the hybridization and ligation of the second group of probes are performed. There are 4 different bases at the second position of the 5'-terminal of the second group of probes, and there are random sequences at the other positions. After that, the fluorescent molecule at the second position is detected to determine the sequence at the second position. Similarly, the base sequences at positions 3 to 8 are determined, respectively. A total of 8 groups of probes are used to determine the sequence of the first eight bases, and then longer new sequencing primers are added to carry out the sequencing of the next eight bases.

The ligation sequencing method of ABI is called as Sequencing by Oligonucleotide Ligation and Detection (SOLiD), which uses 16 different groups of probes. The first two bases of each group of probes are fixed sequences, the next three bases are a random sequence, and the following three bases are universal bases; the method for ligating random bases and universal bases (5th and 6th) is O—P—S, and the above sequences can be sorted from the 5'-terminal or the 3'-terminal. As shown in the following formula I, if sorted from the 5'-terminal, the 3'-terminal of the random base is an oxygen atom, and the 5'-terminal of the first universal base is a sulfur atom. Similarly, if sorted from the 3'-terminal, the 5'-terminal of the third random base is an oxygen atom, and the 3'-terminal of the first universal base is a sulfur atom.

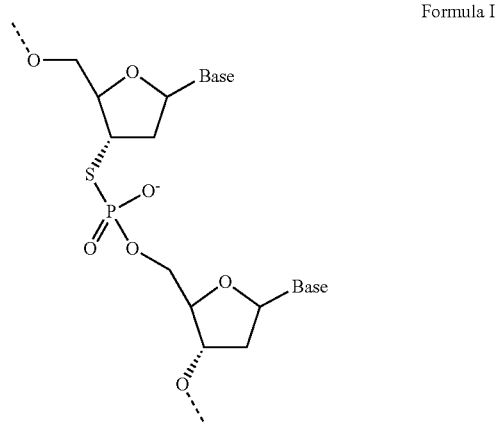

Formula I

The sequencing is performed from the 3'-terminal to the 5'-terminal: a sequencing primer is added, a sequencing probe is used for ligation and detection; in the ligation reaction system, the template and primers are complementarily paired, the primers are connected to magnetic beads and photographed directly. Silver ions are used for excision (silver ions can specifically bind with sulfur elements to cleave S—P bond, and P is connected to hydroxide ions and S is connected to silver ions after the cleavage), so that all universal bases are excised, a phosphate group is remained at the 5'-terminal direction, and ligation is carried at the position after 5 bases in the next cycle. After multiple repeating, the sequencing strand is removed and a new primer is hybridized thereon, wherein the new primer has one more base than the previous one; after multiple repeating the cycle again, the sequencing strand is removed and the primer for the third time is hybridized thereon. In this way, after multiple repeating, the entire sequence can be ligated, and the sequence information of each position can be determined through the cross-comparison of the signals.

The method of sequencing-by-ligation has the following shortcomings: (1) due to the large number and many kinds of probes, the cost is relatively high; (2) since 5 bases should be added each time in the SOLiD method, the sequencing primers have to be reloaded after one or several cycles, which increases the sequencing cost and time cost; (3) the excision method is not friendly to the sequencing system. As a biochemical reaction in the sequencing, many enzymes are very sensitive to transition metals. In addition, the used silver ions are prone to being resided and will inevitably affect the subsequent experiments. For example, the reaction buffer may contain chloride ions, while silver ions are easily reacted with them to generate precipitation. In addition, silver ions may also react with T bases to form a mismatch of T-Ag-T structure.

The method of sequencing-by-synthesis of Illumina uses a reversibly blocked group to modify the 3'-terminal hydroxyl and a fluorescent dye reversibly attached to the base (as shown in FIG. 1). One base is polymerized in each cycle, the fluorescent signal at this position is detected to determine the base information. After the base information is determined, the 3'-terminal blocking group and the fluorescent dye on the base are excised, and the 3'-terminal blocking group and the group of the base to which the fluorescent dye is attached are of the same type, and thus these groups can be excised simultaneously.

However, in the method of Illumina, the blocking uses azidomethylene mode, the excision uses organic phosphine (as shown in FIG. 2), there is a long-chain ligation between the dye and the base, and an azidomethylene derivative is designed in the long chain. After the excision, like the 3'-terminal, the linking group also has a hydroxyl group, and there are dozens of atoms besides the hydroxyl group (as shown in FIG. 3).

Although the sequencing-by-synthesis is currently very successful, some ligating groups, also known as scars, still remain on the base after the fluorophores ligated to the base are removed. On the one hand, scar atom may affect the reads of the sequencing, and on the other hand, it may affect the signal of the next base; in addition, dNTP is not easily recognized by polymerase due to the over-modification (at the 3-terminal and the base), and a lot of work is needed to adapt the polymerase so as to reach the usable standard (The history and advances of reversible terminators used in new generations of sequencing technology. *Genomics Proteomics Bioinformatics.* 2013 February; 11 (1): 34-40).

The sequencing-by-synthesis method has insufficient reads due to the over-modification of scar atoms and bases. In addition, the over-modified dNTP is one of the biggest factors that lead to an increased sequencing cost.

Therefore, there is still a need to develop a new nucleic acid sequencing method, especially a new nucleic acid sequencing method with higher efficiency, longer sequencing reads, higher accuracy, and lower cost.

Contents of the Present Invention

After intensive research and creative labor, the inventors skillfully designed a method for sequencing nucleic acid. The inventors creatively combined the sequencing-by-ligation method and the reversibly blocked dNTP polymerization reaction, which can effectively remove a scar atom, is conducive to improve the reads of sequencing, significantly reduces the cost of sequencing, and shortens the time for sequencing. The following inventions are thus provided:

One aspect of the present invention relates to a method for sequencing nucleic acid, comprising the following steps:

(1) hybridizing a sequencing primer to a nucleic acid molecule to be tested;

(2-1) ligating a nucleic acid probe to the sequencing primer;

(3) detecting the detectable label being bound to the nucleic acid probe of the nucleic acid molecule to be tested, and obtaining information of a base to be tested;

(4-1) ligating a dNTP having a blocking group ligated to the 3'-terminal thereof to a sequencing primer to which a nucleic acid probe is not ligated;

(5) detecting the detectable label being bound to the nucleic acid probe of the nucleic acid molecule to be tested, and obtaining information of a base to be tested;

(6-1) excising the blocking group ligated to the 3'-terminal of the dNTP; preferably, further excising the remaining nucleotides on the nucleic acid probe that are not bound to the base to be tested;

wherein,
when the step (3) exists, the step (5) does not exist; or
when the step (5) exists, the step (3) does not exist;
preferably, the above steps (2-1) to (5) are repeated, or the above steps (2-1) to (6-1) are repeated.

In some embodiments of the present invention, between the step (2-1) and the step (3), the following step is further included:

(2-2) eluting the nucleic acid probes that are not ligated to the nucleic acid molecule to be tested.

In some embodiments of the present invention, between the step (4-1) and the step (5), the following step is further included:

(4-2) eluting the dNTPs that are not ligated to the nucleic acid molecule to be tested.

In some embodiments of the present invention, after the step (6-1), the following step is further included:

(6-2) eluting the portion that is excised in the step (6-1); preferably, the above steps (2-1) to (6-2) are repeated.

In some embodiments of the present invention, in the step (2-1), for the sequencing primers that are hybridized to the nucleic acid molecule to be tested, only a part of the sequencing primers are ligated to the nucleic acid probe, and the "part" may be, for example, 10% to 90%, 10% to 80%, 10% to 70%, 10% to 60%, 10% to 50%, 10% to 40%, 10% to 30%, 10% to 20%, 20%-90%, 20% to 80%, 20% to 70%, 20% to 60%, 20% to 50%, 20% to 40%, 20% to 30%, 30% to 90%, 30% to 80%, 30% to 70%, 30% to 60%, 30% to 50%, 30% to 40%, 40% to 50%, 40% to 60%, 40% to 70%, 20%, 30%, 40% %, 50%, 60% or 70%.

In some embodiments of the present invention, in the step (2-1), the time for the ligating is determined according to the following method: the signal intensity of the detectable label on the nucleic acid probe ligated to the sequencing primer is sufficiently strong so that it can be detected.

In some embodiments of the present invention, in the step (2-1), the time for the ligating is 0.5 to 30 minutes, preferably 1 to 10 minutes, more preferably 2 to 6 minutes, and particularly preferably 4 minutes.

In some cases, when the time for the ligating is longer than 10 minutes, the time cost of sequencing will increase.

In some cases, when the time for the ligating is less than 1 minute, it may result in insufficient ligation efficiency, and the signal strength of the detectable label on the nucleic acid probe cannot be fully detected, which affects the sequencing quality.

In some embodiments of the present invention, in the step (2-1), the temperature for the ligating is an appropriate temperature at which the ligase being used works, for example, 16° C. to 37° C.; preferably, the optimal temperature of the ligase, such as 25° C.

In some embodiments of the present invention, the eluting conditions of any two of the steps (2-2), (4-2) and (6-2) are the same, or the eluting conditions of the three steps are the same.

In some embodiments of the present invention, in the step (4-1), the dNTP used has no detectable label.

In some embodiments of the present invention, in the step (4-1), the dNTP is ligated by a polymerase-catalyzed polymerization reaction to the sequencing primer that is not ligated to the nucleic acid probe; preferably, the polymerization reaction is completed. In some embodiments of the present invention, preferably, the polymerization is performed for a time of 0.5 to 10 minutes, preferably 2 minutes; the polymerization reaction is performed at 45° C. to 60° C.; preferably 55° C.

In some embodiments of the present invention, in the step (6-1), the conditions for excising the blocking group ligated to the 3'-terminal of the dNTP and the conditions for excising the remaining nucleotides on the nucleic acid probe that are not bound to the base to be tested are the same.

In some embodiments of the present invention, the nucleic acid probe comprising a first moiety, a second moiety, a linker and a detectable label, wherein:

the first moiety has a sequencing base, which is one or more selected from the group consisting of A, T, U, C and G, the second moiety has random bases and/or universal bases, and the number of the bases is at least 3, the first moiety is ligated to the second moiety via the linker, and the ligation between the first moiety and the linker can be cleaved, and the detectable label is ligated to the second moiety or the linker.

In some embodiments of the present invention, the first moiety is located at the 5'-terminal or the 3'-terminal.

In the present invention, unless otherwise specified, the nucleic acid probe is also simply referred to as a probe.

In the present invention, the first moiety and the second moiety are only used for clarity and have no sequential meaning.

In the present invention, the first moiety is a sequencing base.

In one embodiment of the present invention, the first moiety is located at the 5'-terminal or the 3'-terminal; preferably, the first moiety is located at the 5'-terminal. If the first base at the 3'-terminal of the probe is a sequencing base, the detectable label and/or the chemical group can be designed at the 5'-terminal; otherwise, if the first base at the 5'-terminal is a sequencing base, the detectable label and/or the chemical group can be at the 3'-terminal.

a length determined by taking into account the stability of hybridization between the probe and template and the cost for synthesis of the probe.

The end of the second moiety is blocked, which means that there is not a free 3'-OH at the terminal of the second moiety, so it cannot form a new 3',5'-phosphodiester bond, that is, it cannot be ligated to another probe.

In one embodiment of the present invention, when the ligation between the first moiety and the linker is cleaved, the 3'-terminal OH or 5'-terminal phosphate group of the first moiety is exposed.

In one embodiment of the present invention, when the ligation between the first moiety and the linker is cleaved, the second moiety and the linker are removed.

In one embodiment of the present invention, preferably, the detectable label is ligated to the second moiety;

preferably, the detectable label is ligated to 3'-OH at the terminal of the second moiety;

preferably, the detectable label is ligated to 3'-OH at the terminal of the second moiety by a phosphate bond.

In some embodiments of the present invention, wherein the detectable label is a fluorophore, preferably at least one selected from the group consisting of cy3, cy5, Texas Red, 6-FAMTM, AF532, AF647 and AF688; preferably, the fluorophore is ligated to 3'-OH at the terminal of the second moiety; preferably, the fluorophore is ligated to 3'-OH at the terminal of the second moiety via a phosphate bond. The probe is now blocked. For example, the following Formula II or Formula III is shown:

Formula II

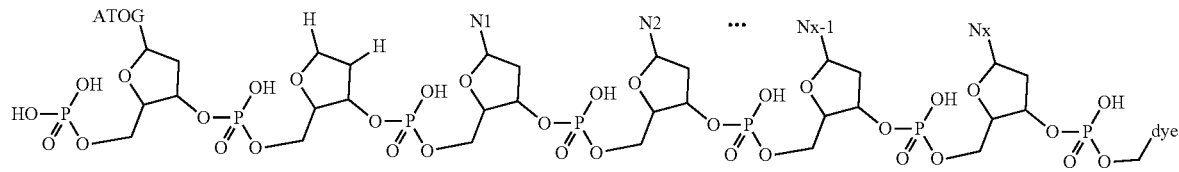

In one embodiment of the present invention, the bases of the second moiety are random bases.

In one embodiment of the present invention, the bases of the second moiety are universal bases.

In Formula II, 5' is a sequencing base, and 3' is a fluorophore.

In the following Formula III, 3' is a sequencing base, and 5' is a fluorophore.

Formula III

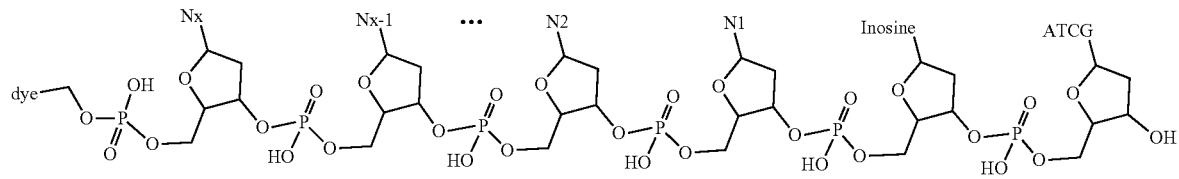

In one embodiment of the present invention, the bases of the second moiety are both random bases and universal bases.

In some embodiments of the present invention, the bases of the second moiety are 3 to 15 bases, preferably 5 to 12 bases, and more preferably 5 to 10 bases (for example, 5, 6, 7, 8, 9, or 10 bases), particularly preferably 6 to 9 bases. Without being bound by any theory, the preferred probe has The ligation between the first moiety and the linker can be cleaved in different ways, so that the 3'-terminal OH or 5'-terminal phosphate group can be exposed for the next cycle of sequencing reactions.

In some embodiments of the present invention, the linker does not contain a sulfur atom; preferably, the linker is selected from the group represented by the following Formula IV to Formula IX:

Formula IV

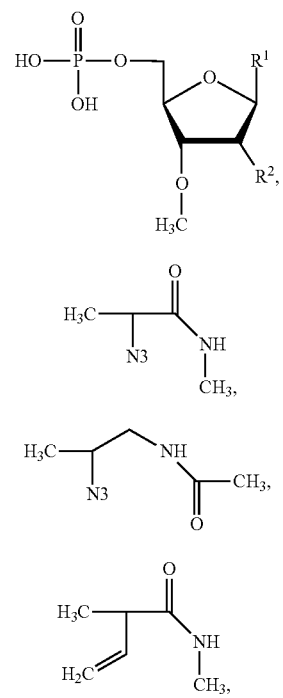

and

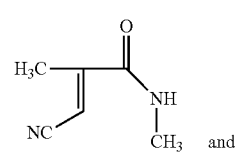

wherein, in Formula IV, $R^1$ is selected from the group consisting of H, OH, $C_1$-$C_6$ alkyl, $C_2$-$C_6$ alkenyl, and $C_2$-$C_6$ alkynyl; $R^2$ is selected from the group consisting of H, OH, F, Cl, and Br.

The ligation modes represented by the groups of the above Formula IV to Formula IX are abbreviated as AP site, azide, azide, allyl, cyanovinyl and inosine sites, respectively. The excision methods in sequence are Endonuclease IV, organic phosphine, organic phosphine, palladium catalyst, organic phosphine, and hAAG enzyme+endonuclease IV, respectively.

The methods for ligation and excision of the groups represented by the Formula IV to Formula IX can be methods known to those skilled in the art, and may also refer to the following description.

(1) AP site ligation mode

The sequencing base and the second base (N1) are ligated using a cyclic deoxyribose or deoxyribose derivative, and a specific ligation method may refer to Xipeng Liu, Jianhua Liu. The mechanism of base excision repair in *Chlamydiophda pneumoniae*. DNA Repair 4 (2005) 1295-1305. The above Formula X is a structural formula with 5'-terminal sequencing base, wherein $R^1$ is selected from the group consisting of H, OH, $C_1$-$C_6$ alkyl, $C_2$-$C_6$ alkenyl and $C_2$-$C_6$ alkynyl; $R^2$ is selected from the group consisting of H, OH, F, Cl and Br.

Formula XI is a reversibly blocked non-fluorescently modified dNTP used in the polymerization reaction.

(2) Azide ligation mode

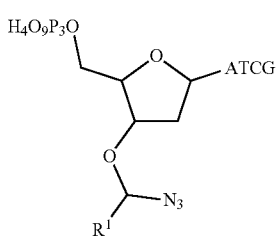

Formula XV

The method for ligation between the chemical group and the sequencing base in Formula XII, Formula XIII or Formula XIV may refer to the prior art, for example, U.S. Pat. No. 8,084,590 B2.

The ligation between the chemical group and the sequencing base in Formula XII, Formula XIII or Formula XIV may be cleaved by an organic phosphine (e.g., THPP, TCEP). The conditions for excision may be, for example, 100 mM TCEP, pH=7, 1 M sodium chloride, 5 minutes at 50° C.

Formula XV is a reversibly blocked non-fluorescently modified dNTP used in the polymerization reaction.

In some embodiments of the present invention, in the step (4-1), the blocking group is selected from the following Formula A to Formula D:

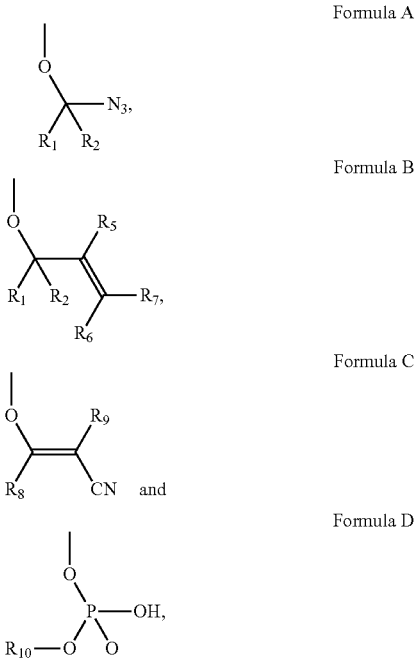

Formula A

Formula B

Formula C

Formula D wherein:
in Formula A, $R^1$ and $R^2$ are independently selected from the group consisting of H, F, $CF_3$, $CHF_2$, $CH_2F$, $CH_2R$ alkane, COOR and CONHR, wherein R is independently $C_1$-$C_6$ alkyl;

in Formula B, $R_3$ to $R_7$ are independently selected from the group consisting of H and $C_1$-$C_6$ alkyl;

in formula C, $R_8$ and $R_9$ are independently selected from the group consisting of H, F, $C_1$, $CF_3$, nitro, cyano, $C_1$-$C_6$ alkoxy and $C_1$-$C_6$ carboxyl;

in Formula D, $R_{10}$ is selected from $C_1$-$C_6$ alkyl.

In one embodiment of the present invention, the nucleic acid molecule to be tested in the step (1) is ligated to a solid support.

The solid support includes, but is not limited to, a chip, a flow cell, a magnetic bead, and the like. A linker sequence is fixed on the solid support, and the linker sequence is capable of binding to the nucleic acid molecule to be tested. For example, when the nucleic acid molecule to be tested is in the form of a DNA library, the linker sequence is ligated to the linker sequence for constructing the library through base pairing. The method for constructing the DNA library may be a method known to those skilled in the art.

Preferably, the method for sequencing a nucleic acid further comprises a step of amplifying the nucleic acid molecule to be tested that is ligated to the solid support.

Without being bound by any theory, the purpose of amplification is to obtain a sufficient number of samples and amplify the signal intensity of the bases so as to achieve the signal requirements for the sequencing. The amplification products are also ligated to the solid phase, thereby forming a local enrichment.

The method for the amplification may be a polymerase chain reaction (PCR), for example, Emulsion PCR or bridge PCR. The emulsion PCR may refer to, for example, the emulsion PCR operation in the SoLiD sequencing method of ABI company, or refer to the emulsion PCR operation in the Roche 454 sequencing method. The bridge PCR may refer to the bridge PCR operation in the Solexa sequencing method of Illumina company.

In one embodiment of the present invention, the ligation of the probe in the step (2-1) is the same as other sequencing-by-ligation, and it is a universal T4 DNA ligase ligation reaction.

In one embodiment of the present invention, in the steps (2-2), (4-2) and/or (6-2), the reagent used for elution may be a reagent known to those skilled in the art, for example, 5×SSC+0.05% tween 20.

In an embodiment of the present invention, in the step (6-1), after the ligation between the first moiety of the nucleic acid probe and the linker is excised, the 3'-terminal OH is exposed, and the next cycle of sequencing-by-ligation can be performed (see FIG. 4).

Normally, the steps (2-1) to (6-1) or the steps (2-1) to (6-2) are repeated; if a round of sequencing has been completed, only the steps (2-1) to (5) may be repeated.

Another aspect of the present invention relates to a kit for nucleic acid sequencing, comprising:
a nucleic acid probe, a ligase, a dNTP having a blocking group ligated to the 3'-terminal thereof, and a polymerase;
Reagent 1 for excising the blocking group ligated to the 3'-terminal of dNTP; and
Reagent 2 for excising the remaining nucleotides on the nucleic acid probe that are not bound to the base to be tested;
preferably, Reagent 1 and Reagent 2 are the same;
preferably, the kit further comprises an appropriate buffer, such as a buffer for dissolving the nucleic acid probe;
preferably, the kit further comprises an appropriate eluent; for example, Eluent 1 for eluting the nucleic acid probe; for example, Eluent 2 for eluting dNTP; preferably, Eluent 1 and Eluent 2 are the same.

In some embodiments of the present invention, the nucleic acid probe comprises a first moiety, a second moiety, a linker and a detectable label, wherein:
the first moiety has a sequencing base, which is one or more selected from the group consisting of A, T, U, C and G,
the second moiety has random bases and/or universal bases, and the number of the bases is at least 3, the first moiety is ligated to the second moiety via the linker, and the ligation between the first moiety and the linker can be cleaved, the detectable label is ligated to the second moiety or to the linker.

In one embodiment of the present invention, the first moiety is located at the 5'-terminal or the 3'-terminal.

In some embodiments of the present invention, the bases of the second moiety are 3 to 15 bases, preferably 5 to 12 bases, and more preferably 5 to 10 bases (for example, 5, 6, 7, 8, 9, or 10 bases), particularly preferably 6 to 9 bases.

In some embodiments of the present invention, wherein the detectable label is a fluorophore, preferably at least one selected from the group consisting of cy3, cy5, Texas Red, 6-FAMTM, AF532, AF647 and AF688;

preferably, the detectable label is ligated to the second moiety;

preferably, the detectable label is ligated to 3'-OH at the terminal of the second moiety;

preferably, the detectable label is ligated to 3'-OH at the terminal of the second moiety by a phosphate bond.

In some embodiments of the present invention, the linker does not contain a sulfur atom; preferably, the linker is selected from the group represented by the following Formula IV to Formula IX:

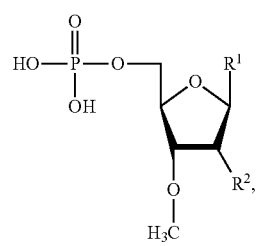

Formula IV

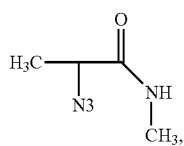

Formula V

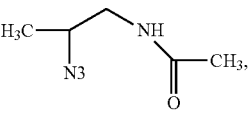

Formula VI

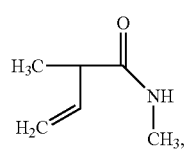

Formula VII

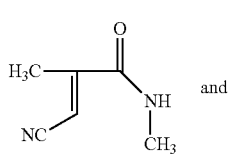

Formula VIII and

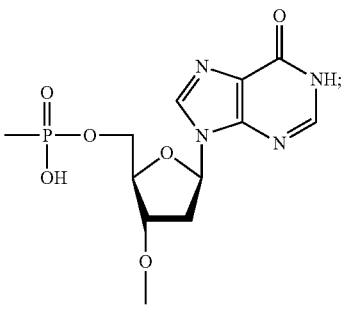

Formula IX wherein, in Formula IV, IV is selected from the group consisting of H, OH, $C_1$-$C_6$ alkyl, $C_2$-$C_6$ alkenyl, and $C_2$-$C_6$ alkynyl; $R^2$ is selected from the group consisting of H, OH, F, Cl, and Br.

In some embodiments of the present invention, the ligase is a DNA ligase, and the polymerase is a DNA polymerase.

In some embodiments of the present invention, the kit is characterized by any one or more of the following items 1) to 4):

1) the DNA ligase is one or more selected from the group consisting of T4 DNA ligase, T7 DNA ligase, and T3 DNA ligase;

2) the concentration of the nucleic acid probe is 0.1 μM to 5 μM, preferably 1 μM;

3) the concentration of the DNA ligase is 0.01 μM to 2 μM, preferably 0.5 μM.

4) the reagents in the kit are free of silver ions.

In some embodiments of the present invention, Reagent 1 or Reagent 2 is an endonuclease (e.g., endonuclease IV or endonuclease V), an organic phosphine (e.g., THPP or TCEP), or a complex of $PdCl_2$ and sulfonated triphenylphosphine.

In one embodiment of the present invention, the specially designed probes are used to achieve rapid ligation and polymerization, shorten the excision time, reduce time cost, reduce damage to the sequencing system, eliminate scar atoms, and make the sequencing chain be natural 4 kinds of bases, and eventually increase the reads, which is called as combination sequencing.

The inventors have further discovered in research that, especially when the base on which the scar atom is located is G, it affects the accuracy of the base next to the G base, which is shown by the experimental results of Experimental Example 1.

In the present invention, the nucleic acid molecule to be tested may be a single-stranded or double-stranded DNA molecule, or a single-stranded or double-stranded RNA molecule. The DNA molecule may be a DNA molecule from an animal, a plant, or a microorganism. Preferably, the DNA molecule is in the form of a DNA library, and the DNA library may be a DNA library constructed using a library construction kit.

In the present invention, Nx means that there are x N bases, and x may be a positive integer, such as 3, 4, 5, 6, 7, 8, 9, . . . 14, 15, and the like.

The term "random base" means that each of the 4 bases occupies 25% of the position.

The term "universal base" means that the base can form a base-pairing structure with any one of the 4 kinds of AGTC, such as 5-nitroindole ring, 2-nitropyrrole ring, and the like.

The term "sequencing base" means that the base at the position is a fixed base, for example, if the base at the position is T, the probe is responsible for detecting base A.

In the present invention, the term "$C_1$-$C_6$ alkyl" refers to a straight or branched alkyl having 1 to 6 carbon atoms, such as methyl, ethyl, propyl, isopropyl, n-butyl, sec-Butyl, tert-butyl, pentyl, 2-pentyl, isopentyl, neopentyl, hexyl, 2-hexyl, 3-hexyl, etc.; $C_1$-$C_4$ alkyl and $C_1$-$C_3$ alkyl can be understood similarly. The preferred alkyl group is a $C_1$-$C_4$ alkyl, and the more preferred alkyl group is a $C_1$-$C_3$ alkyl.

The term "$C_2$-$C_6$ alkenyl" refers to an alkenyl having 2 to 6 carbon atoms and at least one double bond, and includes vinyl, propenyl, 1-but-3-enyl, 1-pent-3-enyl, 1-hex-5-enyl, etc.; $C_3$-$C_5$ alkenyl can be similarly understood. $C_3$-$C_5$ alkenyl is preferred.

The term "$C_2$-$C_6$ alkynyl" refers to a hydrocarbon group having 2 to 6 carbon atoms and at least one triple bond, and includes ethynyl, propynyl, butynyl, pentyn-2-yl, etc.; $C_3$-$C_5$ alkynyl can be understood similarly. $C_3$-$C_5$ alkynyl is preferred.

The beneficial effects of the present invention

The present invention or a preferred embodiment thereof has at least one of the following technical effects:

(1) Avoiding the generation of scar atoms during sequencing;
(2) Conducive to improving the reads of sequencing;
(3) Conducive to improving the accuracy of sequencing;
(4) Conducive to shortening the time for sequencing;
(5) Since there is no need to modify dNTP with a label such as a dye, the cost is significantly reduced;
(6) In a preferred embodiment, since the number or types of probes in sequencing is reduced, the cost is also significantly reduced.
(7) In a preferred embodiment, since one base is added at a time through the nucleic acid probe ligation, repeated addition of primers is not required, and the cost is also reduced.
(8) In a preferred embodiment, an excision method that is friendly to the sequencing reaction system is also used.

SPECIFIC MODELS FOR CARRYING OUT THE PRESENT INVENTION

Figure 1:
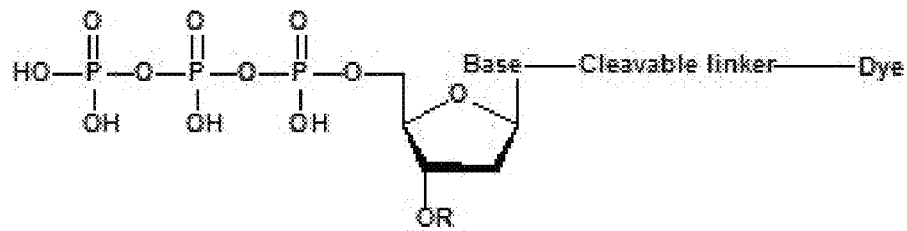
FIG. 1: Schematic structural diagram of the reversibly blocked dNTP used the in sequencing-by-synthesis method.
Figure 2:
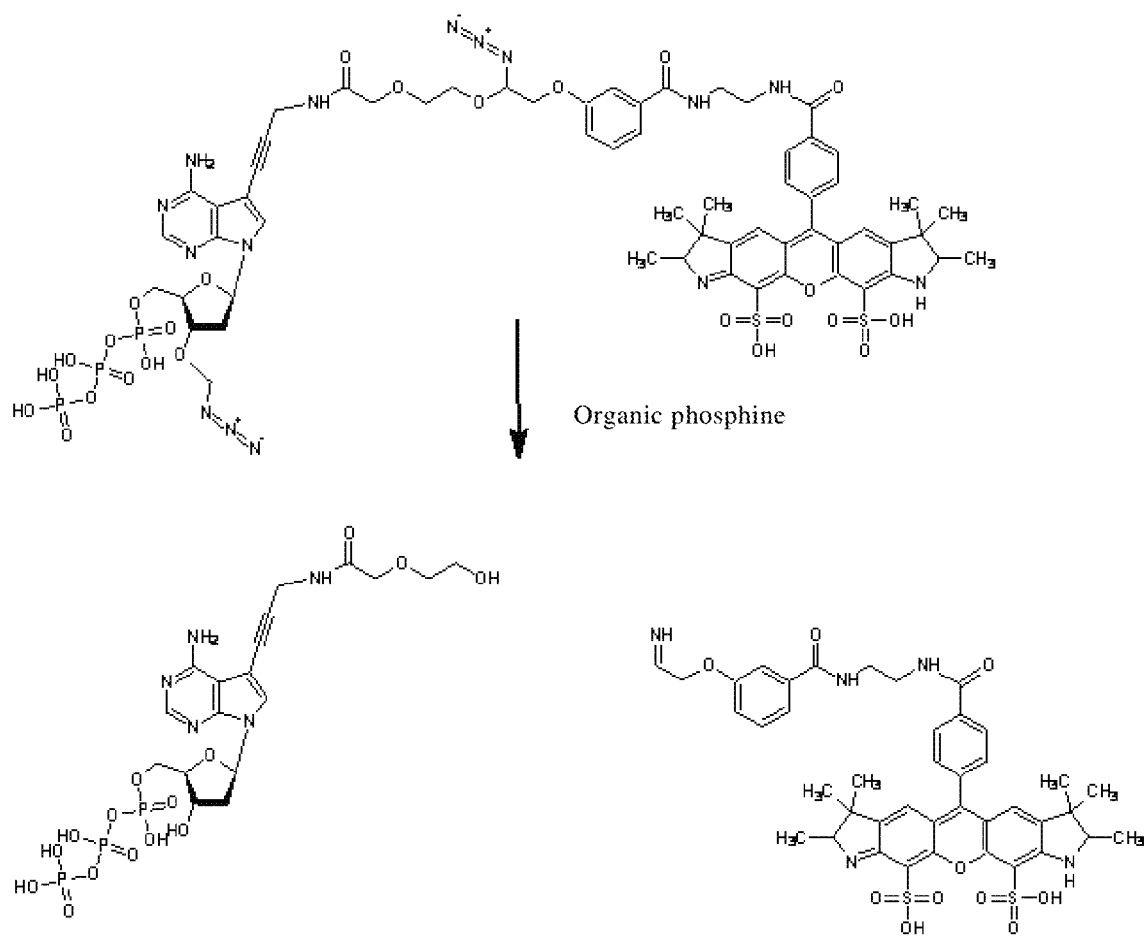
FIG. 2: Schematic diagram of excision chemical reaction in the sequencing-by-synthesis method.
Figure 3:
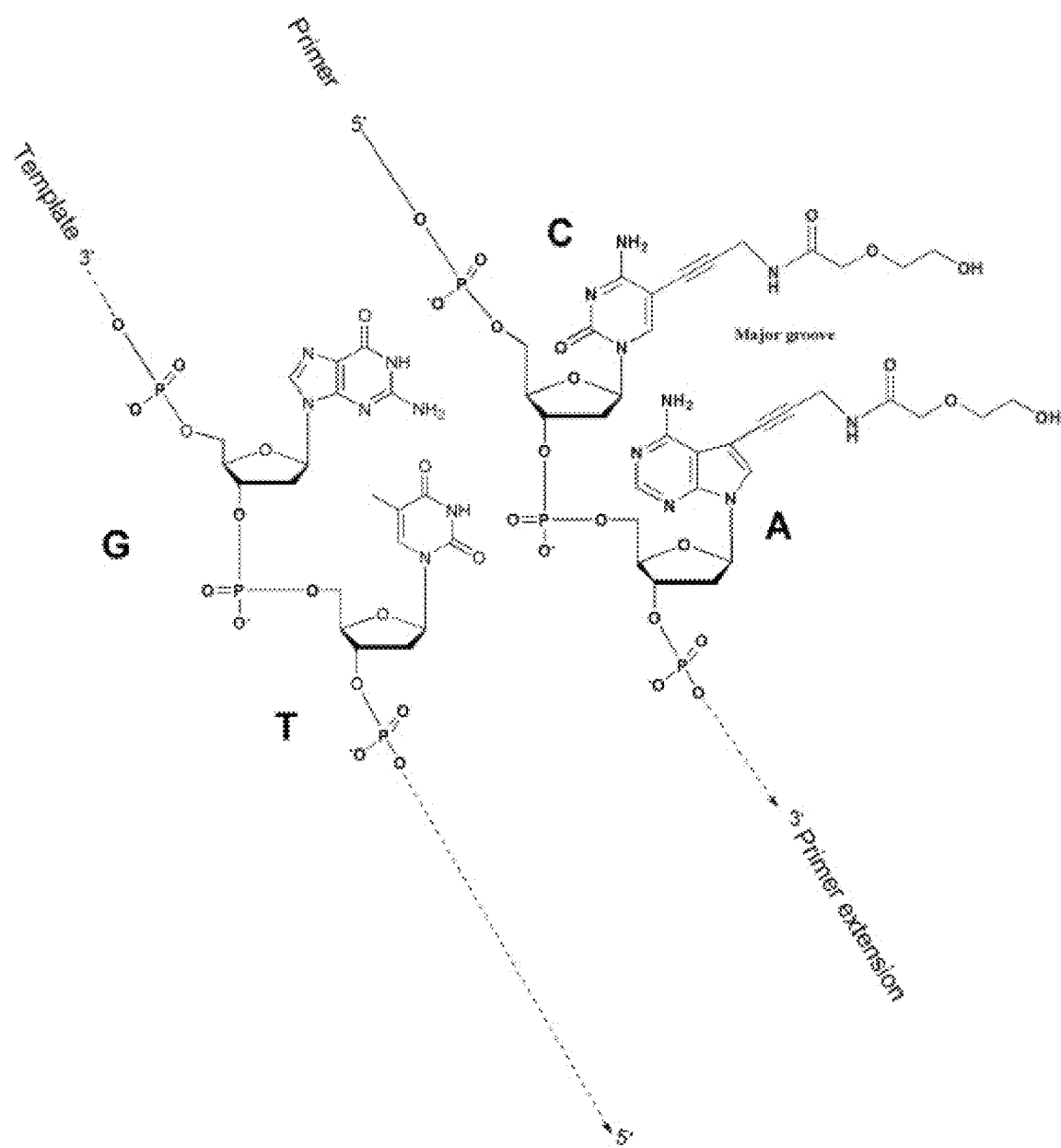
FIG. 3: After the excision reaction in the sequencing-by-synthesis method, the scar atoms left by dNTP on the sequencing chain are reversibly blocked.
Figure 4:
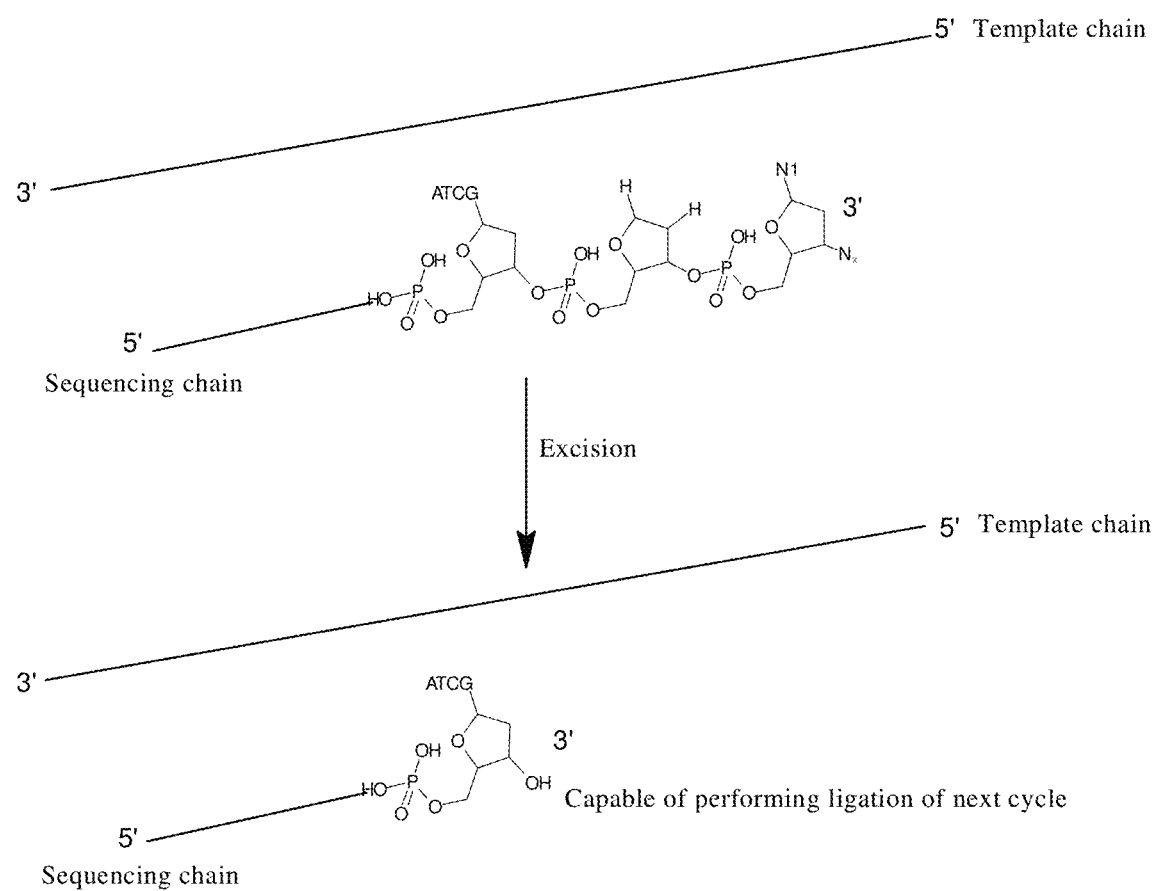
FIG. 4: Schematic diagram of AP site-containing probes removed by endonuclease IV.

The embodiments of the present invention will be described in detail below with reference to examples, but those skilled in the art will understand that the following examples are only used to illustrate the present invention, and should not be considered as limiting the scope of the present invention. If the specific conditions are not indicated in the examples, the conventional conditions or the conditions recommended by the manufacturer are used. If the reagents or instruments used are not specified by the manufacturer, they are all conventional products that are commercially available.

The nucleic acid probes or modified nucleotide used in the following examples can be synthesized according to the methods known in the art, and unless otherwise specified, they are synthesized by a commissioned commercial company, such as Heya Medical Technology (Shanghai) Co., Ltd. or Biotech Biotechnology (Shanghai) Co., Ltd.

Example 1: Sequencing Application of AP Site Reversible Ligation Nucleic Acid Probe (3 Random Bases+3 Universal Bases) in Combination with Phosphate-Blocked Nucleotide (1)

1. Instruments and Reagents

The instrument was based on a BGISEQ-500 platform. Theoretically, other sequencing platforms (such as Illumina's Hiseq platform, etc.) could be appropriately adjusted to perform the same or similar experiments as in this example.

In addition, in order to enable the application on the BGISEQ-500 platform, the selected modified dye had absorption and emission wavelengths similar to those of the dye used by the BGISEQ-500 reagent, so that it could be well detected by the BGISEQ-500 optical system.

Some of the reagents used in this experiment were completely the same as those of BGISEQ-500, for example, the photographic buffer reagent and elution buffer 2 used in this experiment.

Some reagents used in this experiment were different from those of BGISEQ-500, including: a ligation solution containing "the probes, enzymes and buffers of this example", the excision buffer solution of this experiment was used to replace the excision buffer solution of BGISEQ-500; specific components were shown in the Part 2 as follows.

Excision reagent buffer: including 50 mM Tris-HCl, 0.1M NaCl, 2 mM $MgSO_4$, 2 mM DTT, 1 wt % Tween-80, 0.5 wt % tert-butanol, pH 7.5, 0.5 µM endo IV (NEB: M0304S).

Polymerization buffer for the phosphate-blocked nucleotide was as follows: pH 7.8, containing 20 mM sodium chloride, 3 mM magnesium sulfate, 50 mM Tris, 5% DMSO, 0.05% Tween-20, and 0.2 µM KOD156 DNA polymerase.

The experimental sample was the genomic DNA of E. coli, which was a standard sample carried by BGISEQ-500.

According to the manufacturer's instructions, a library for sequencing was prepared by using MGIeasy™ DNA library preparation kit (Shenzhen Huada Zhizao Technology Co., Ltd.) to extract DNA from E. coli standard strains as raw materials, and it was loaded on the sequencing chip.

2. Synthesis of Probes and Phosphate-Blocked Nucleotide

Shenggong Bioengineering (Shanghai) Co., Ltd. was commissioned to synthesize the following 4 groups of AP site reversible ligation probes (3 random bases+3 universal bases), and mychemlab was commissioned to synthesize 4 phosphate-blocked nucleotides.

The first group of probes (A probes): the first moiety, i.e., the sequencing base was A, and the second moiety was 3 random bases+3 universal bases.

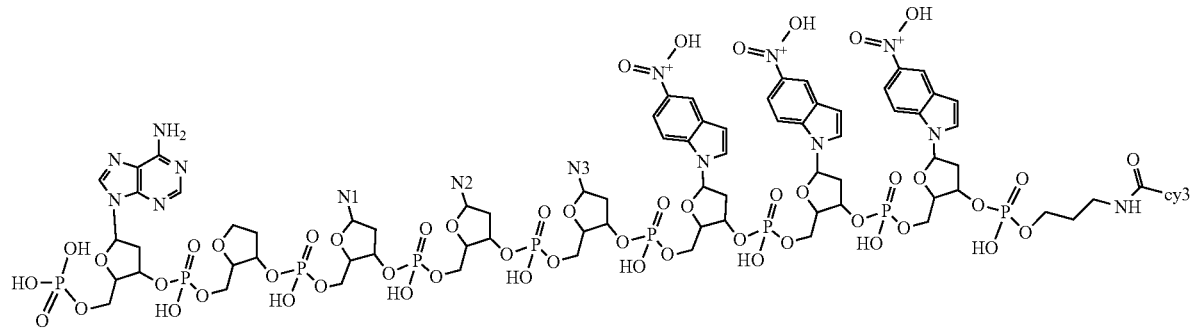

The second group of probes (T probes): the first moiety, i.e., the sequencing base was T, and the second moiety was 3 random bases+3 universal bases.

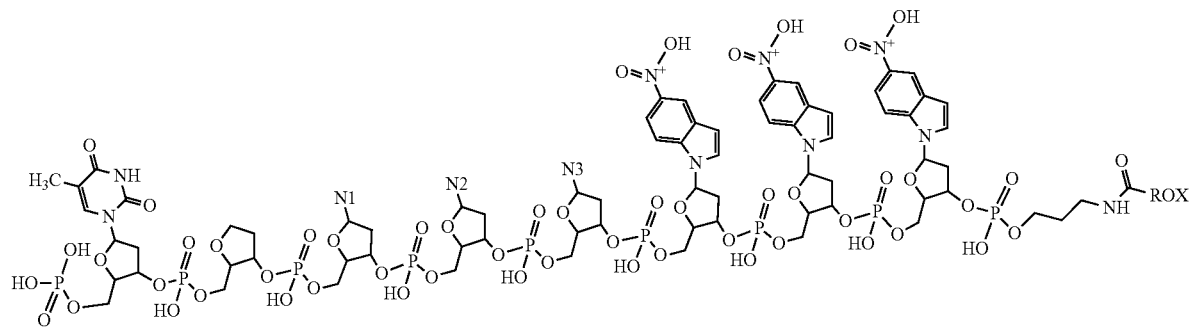

The third group probes (C probes): the first moiety, i.e., the sequencing base was C, and the second moiety was 3 random bases+3 universal bases.

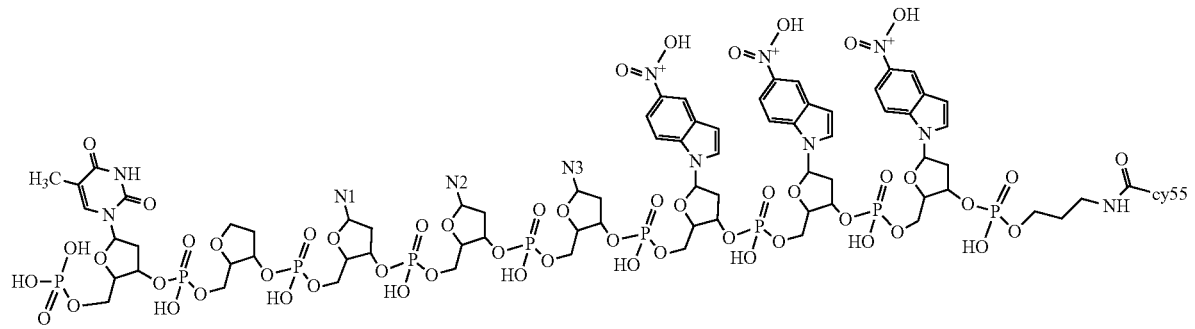

The fourth group probes (G probes): the first moiety, i.e., the sequencing base was G, and the second moiety was 3 random bases+3 universal bases.

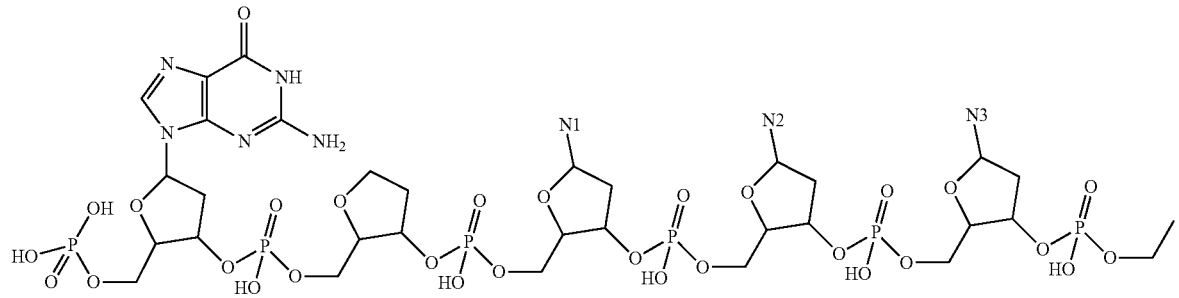

-continued

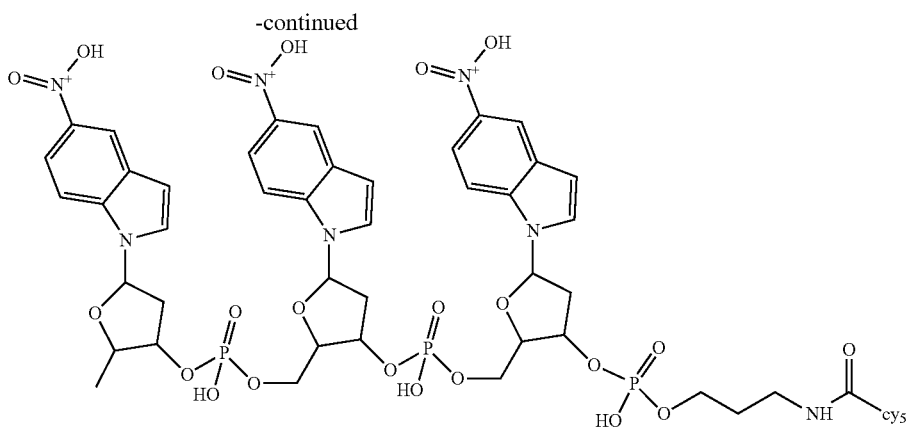

The 4 phosphate-blocked nucleotides were as follows:

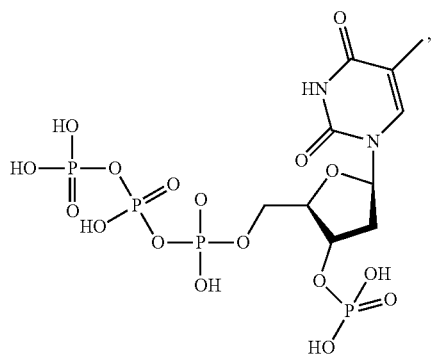

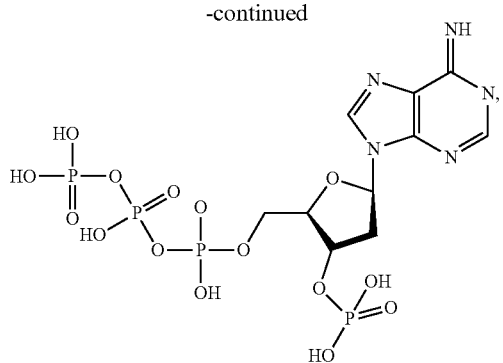

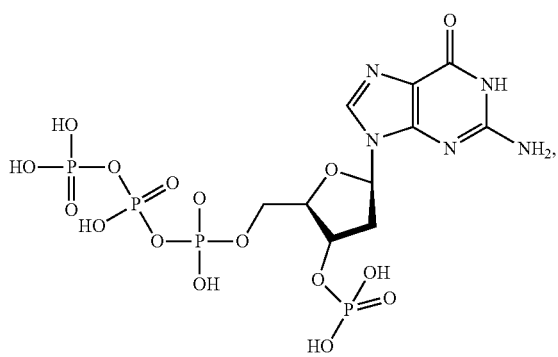

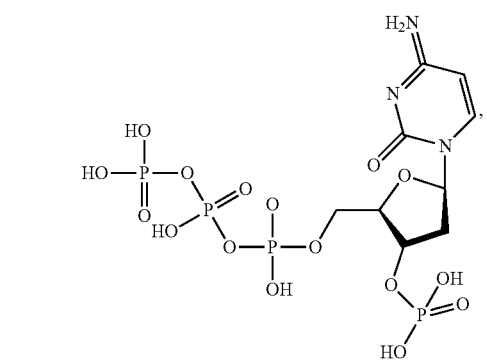

The above 4 groups of probes and T4 DNA ligase were dissolved in the following buffer:

50 mM $CH_3COOK$, 20 mM Tris, 10 mM $Mg(CH_3COO)_2$, 100 μg/ml BSA, 1 mM ATP, 10% PEG6000; to obtain the ligation solution. The concentration of the probe in the ligation solution was 1 μM, in which the molar ratio of A probes:T probes:C probes:G probes was approximately 1:4:4:1. The DNA ligase concentration in the ligation solution was 0.5 μM.

3. Sequencing Steps (1) Referring to the instruction manual of BGISEQ-500, the following preliminary preparations were performed: library construction, a DNA single-stranded loop was amplified into DNA nanospheres, the DNA nanospheres were loaded on the chip carried by BGISEQ-500, and the sequencing primer was loaded on the DNA nanospheres.

(2) The ligation solution containing the above four kinds of probes, T4 DNA ligase and buffer solution was added by using an instrument, and the ligation reaction was performed at 25° C. for 4 minutes;

(3) The elution reagent 2 was used to elute the probes that were not ligated;

(4) The polymerization reaction solution containing the phosphate-blocked nucleotide, polymerase and buffer solution was added, and the polymerization reaction was performed at 55° C. for 2 minutes;

(5) The elution reagent 2 was used to elute unreacted reversibly blocked nucleotides;

(6) The photographic buffer for image acquisition (photographing) was added; the base information of each DNA nanosphere site was analyzed by software;

(7) The endonuclease IV (New England Biolabs, article number M0304L) and its buffer solution were added, and reaction was performed at 37° C. for 5 minutes to excise the AP site and reversibly blocked group, (8) The elution reagent 2 was added to elute the excised portion of the probe and the reversibly blocked group;

The four groups of probes could be added repeatedly for sequencing in the next cycle.

4. Experimental Results

The result was completely consistent with the sequence of the standard sample carried by BGISEQ-500, indicating that the sequencing method of the present invention was accurate.

Example 2: Sequencing Application of AP Site Reversible Ligation Nucleic Acid Probe (3 Random Bases+3 Universal Bases) in Combination with Phosphate-Blocked Nucleotide (2)

This example was performed by following the same method as Example 1, except that the sequencing steps were as follows:

(1) Referring to the instruction manual of BGISEQ-500, the following preliminary preparations were performed: library construction, a DNA single-stranded loop was amplified into DNA nanospheres, the DNA nanospheres were loaded on the chip carried by BGISEQ-500, and the sequencing primer was loaded on the DNA nanospheres.

(2) The ligation solution containing the above four kinds of probes, T4 DNA ligase and buffer solution was added by using instrument, and the ligation reaction was performed at 25° C. for 4 minutes;

(3) The elution reagent 2 was used to elute the probes that were not ligated;

(4) The photographic buffer for image acquisition (photographing) was added; the base information of each DNA nanosphere site was analyzed by software;

(5) The polymerization reaction solution containing the phosphate-blocked nucleotide, polymerase and buffer solution was added, and the polymerization reaction was performed at 55° C. for 2 minutes;

(6) The elution reagent 2 was used to elute unreacted reversibly blocked nucleotides;

(7) The endonuclease IV (New England Biolabs, article number M0304L) and its buffer solution were added, and reaction was performed at 37° C. for 5 minutes to excise the AP site and reversibly blocked group, (8) The elution reagent 2 was added to elute the excised portion of the probe and the reversibly blocked group;

The four groups of probes could be added repeatedly to perform the sequencing in the next cycle.

The result was completely consistent with the sequence of the standard sample carried by BGISEQ-500, indicating that the sequencing method of the present invention was accurate.

Example 3: Sequencing Application of AP Site Reversible Ligation Nucleic Acid Probe (3 Random Bases+3 Universal Bases) in Combination with Phosphate-Blocked Nucleotide (3)

This example was performed by following the same method as Example 1, except that the operation of step (2) was as follows:

The ligation solution containing the above four kinds of probes, T4 DNA ligase and buffer solution was added by using instrument, and the ligation reaction was performed at 25° C. for 1 minute.

The result was completely consistent with the sequence of the standard sample carried by BGISEQ-500, indicating that the sequencing method of the present invention was accurate.

Example 4: Sequencing Application of AP Site Reversible Ligation Nucleic Acid Probe (3 Random Bases+3 Universal Bases) in Combination with Phosphate-Blocked Nucleotide (4)

This example was performed by following the same method as Example 1, except that the operation of step (2) was as follows:

The ligation solution containing the above four kinds of probes, T4 DNA ligase and buffer solution was added by using instrument, and the ligation reaction was performed at 25° C. for 10 minutes.

The result was completely consistent with the sequence of the standard sample carried by BGISEQ-500, indicating that the sequencing method of the present invention was accurate.

Example 5: Sequencing Application of Azido-Ligated Nucleic Acid Probe in Combination with Azidomethylene Blocked Nucleotide This example was performed by following the same method as Example 1, except that the following azido-ligated nucleic acid probe and azidomethylene blocked nucleotide were used:

Four groups of azido-ligated nucleic acid probes:

The first group (A probes): the first moiety, i.e., the sequencing base was A, and the second moiety was 6 random bases.

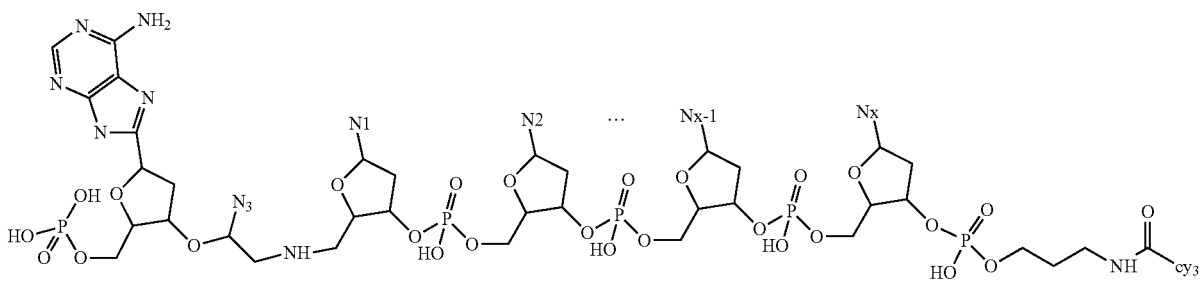

The second group (T probes): the first moiety, i.e., the sequencing base was T, and the second moiety was 6 random bases.

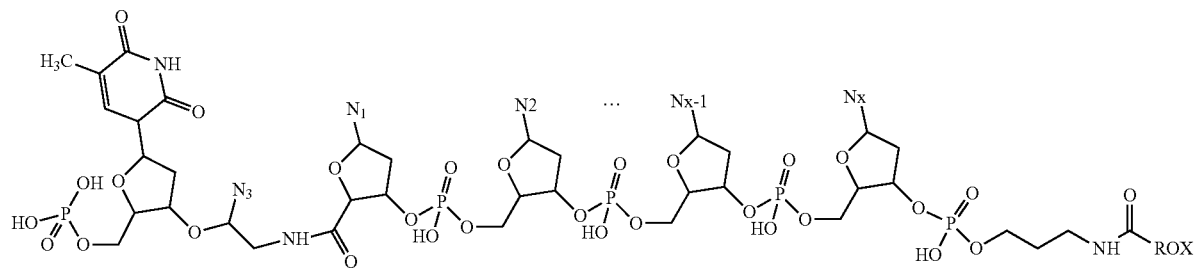

The third group (C probes): the first moiety, i.e, the sequencing base was C, and the second moiety was 6 random bases.

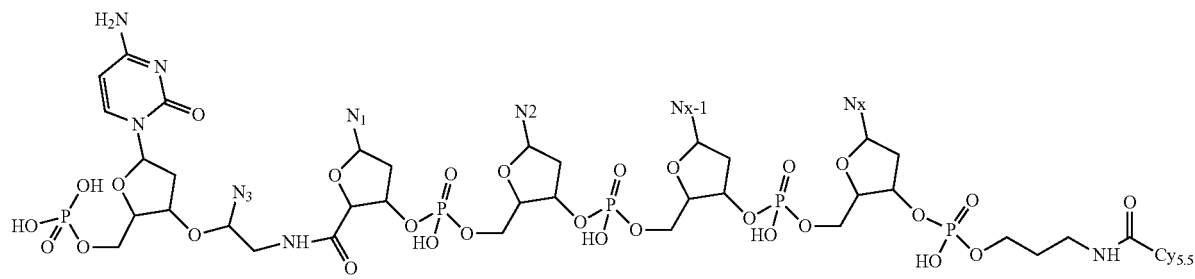

The fourth group (G probes): the first moiety, i.e., the sequencing base was G, and the second moiety was 6 random bases.

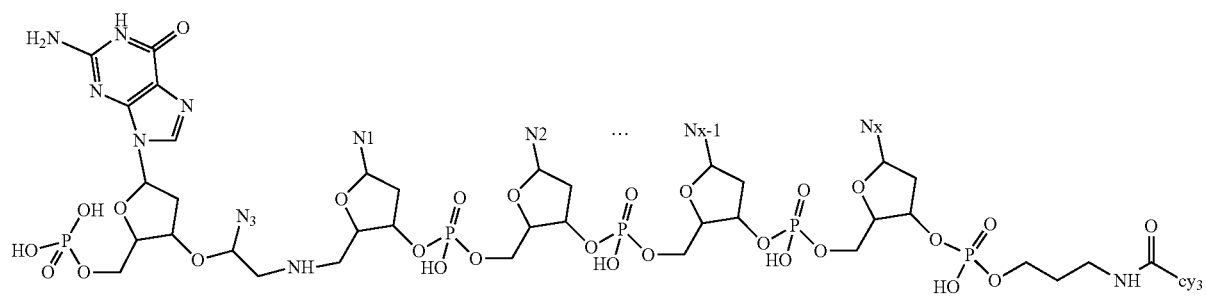

Four azidomethylene blocked nucleotides:

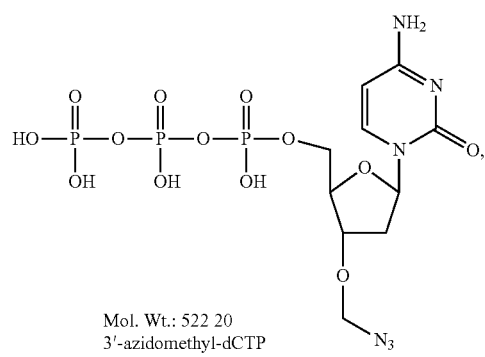

Mol. Wt.: 522 20
3'-azidomethyl-dCTP

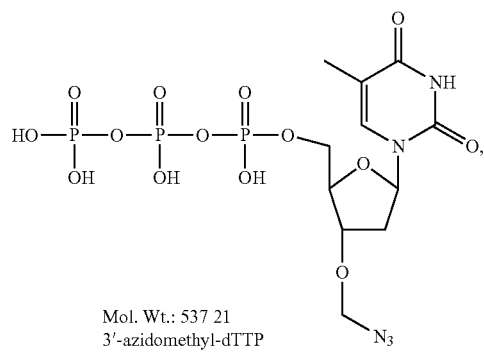

Mol. Wt.: 537 21
3'-azidomethyl-dTTP

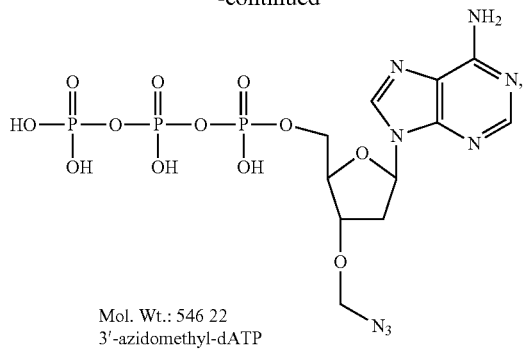

Mol. Wt.: 546.22
3'-azidomethyl-dATP

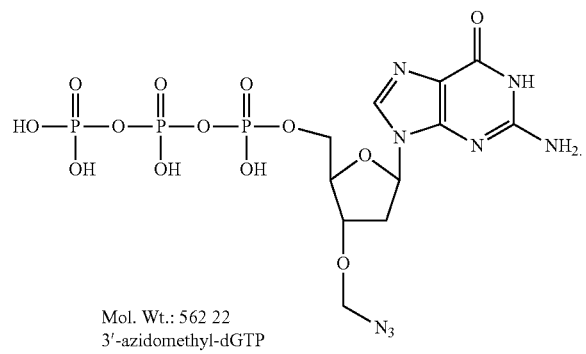

Mol. Wt.: 562.22
3'-azidomethyl-dGTP

The azido-blocked nucleotide polymerization buffer contained 20 mM sodium chloride, 60 mM ammonium sulfate, 3 mM magnesium sulfate, 50 mM Tris, 5% DMSO, 0.05% Tween-20, and the reaction temperature was 55° C., 0.2 μM 9° N DNA polymerase; pH was 9.0.

The excision reagent buffer contained 50 mM Tris-HCl, 1 M NaCl, 10 mM THPP; pH was 9.0.

The results were analyzed using the sequencing analysis software of BGISEQ-500, as shown in Table 1 below.

TABLE 1

| Analysis of sequencing results | |
|---|---|
| Reference Genome (Reference) | E. coli |
| Number of cycles (Cycle Number) | 50 |
| Photographing area (number of areas) | 384 |
| Total reads (Total Reads) | 184.72 M |
| Mapped reads (Mapped Reads) | 160.15 M |
| [a] Q30 | 80.84% |
| Lagging phase (Lag) | 0.34% |
| Leading phase (Runon) | 0.36% |
| Effective reads ratio (ESR) | 79.51% |
| Mapping rate (Mapping Rate) | 86.7% |
| [b] Error rate | 1.13% | a, Q30 indicated the probability of a base being mismeasured was 0.1%, that was, the accuracy was 99.9%; Q30 was 80.84%, which means that the accuracy of 80.84% of the base call reached 99.9%.

b, represented an average error rate.

It could be seen from the above table that the method of the present invention had a Q30 of 80.84%, the error rate was only 1.13%, and the reads reached at least 50, which was better than the existing sequencing-by-ligation method.

Example 6: Sequencing Application of AP Site Reversible Ligation Probe (6 Random Bases) in Combination with Phosphate-Blocked Nucleotide This example was performed by following the same method as Example 1, except that the following 4 groups of nucleic acid probes were used:

Four groups of AP site reversible ligation probes (x=6) were as follows:

The first group (A probes): the first moiety, i.e., the sequencing base was A, and the second moiety was 6 random bases.

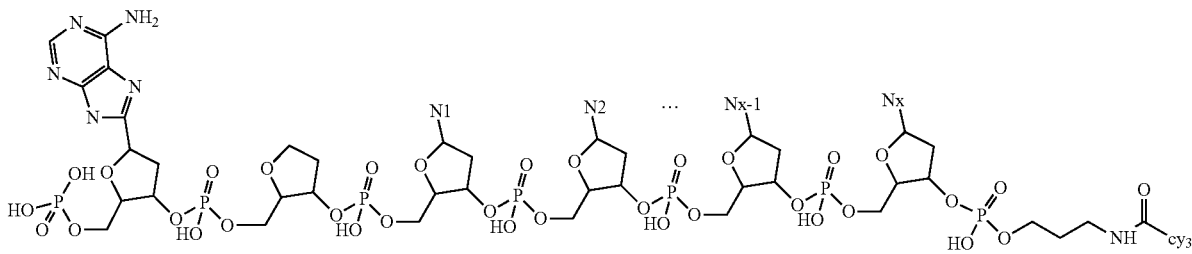

The second group (T probes): the first moiety, i.e., the sequencing base was T, and the second moiety was 6 random bases.

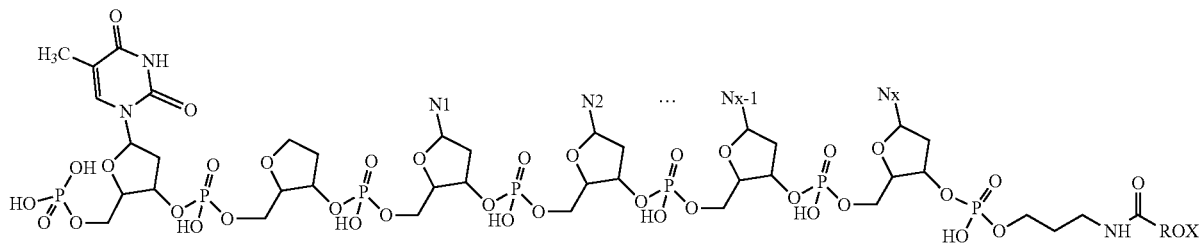

The third group (C probes): the first moiety, i.e., the sequencing base was C, and the second moiety was 6 random bases.

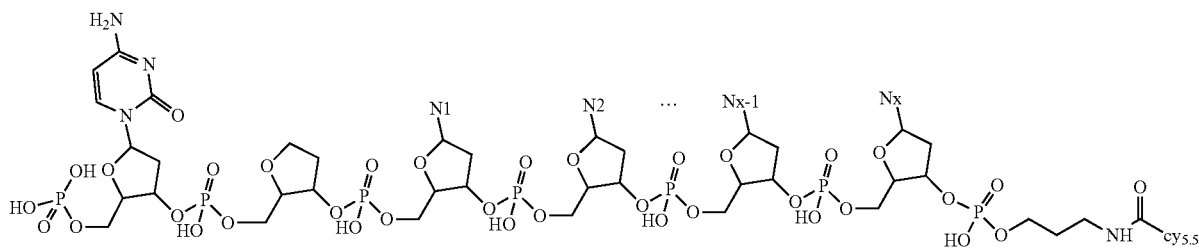

The fourth group (G probes): the first moiety, i.e., the sequencing base was G, and the second moiety was 6 random bases.

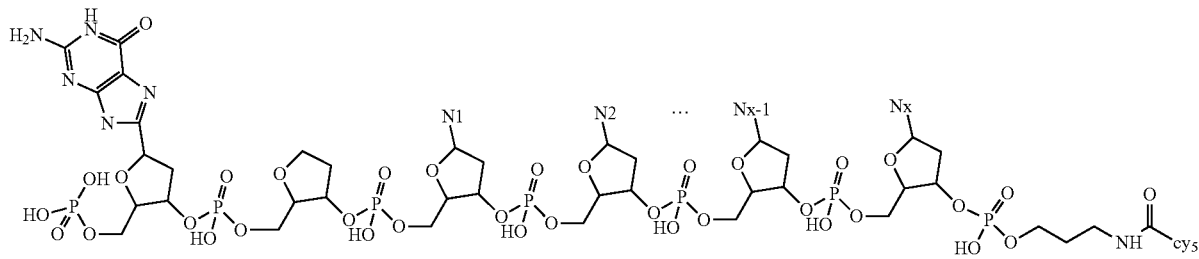

The result was completely consistent with the sequence of the standard sample carried by BGISEQ-500, indicating that the sequencing method of the present invention was accurate.

Example 7: Sequencing Application of AP Site Reversible Ligation Probe (7 Random Bases) in Combination with Phosphate-Blocked Nucleotide This example was performed by following the same method as Example 1, except that the 4 groups of AP site reversible ligation probes were used, wherein x=7.

The result was completely consistent with the sequence of the standard sample carried by BGISEQ-500, indicating that the sequencing method of the present invention was accurate.

Example 8: Sequencing Application of AP Site Reversible Ligation Probe (8 Random Bases) in Combination with Phosphate-Blocked Nucleotide This example was performed by following the same method as Example 1, except that the 4 groups of AP site reversible ligation probes were used, wherein x=8.

The result was completely consistent with the sequence of the standard sample carried by BGISEQ-500, indicating that the sequencing method of the present invention was accurate.

Example 9: Sequencing Application of AP Site Reversible Ligation Probe (9 Random Bases) in Combination with Phosphate-Blocked Nucleotide This example was performed by following the same method as Example 1, except that the 4 groups of AP site reversible ligation probes were used, wherein x=9.

The result was completely consistent with the sequence of the standard sample carried by BGISEQ-500, indicating that the sequencing method of the present invention was accurate.

Experimental Example 1: Effect of Scar on Sequencing

1. Experimental Instruments and Reagents

The four azidomethylene blocked nucleotides were the same as in Example 5.

The four reversibly blocked non-fluorescent nucleotides were as follows (purchased from mychem):
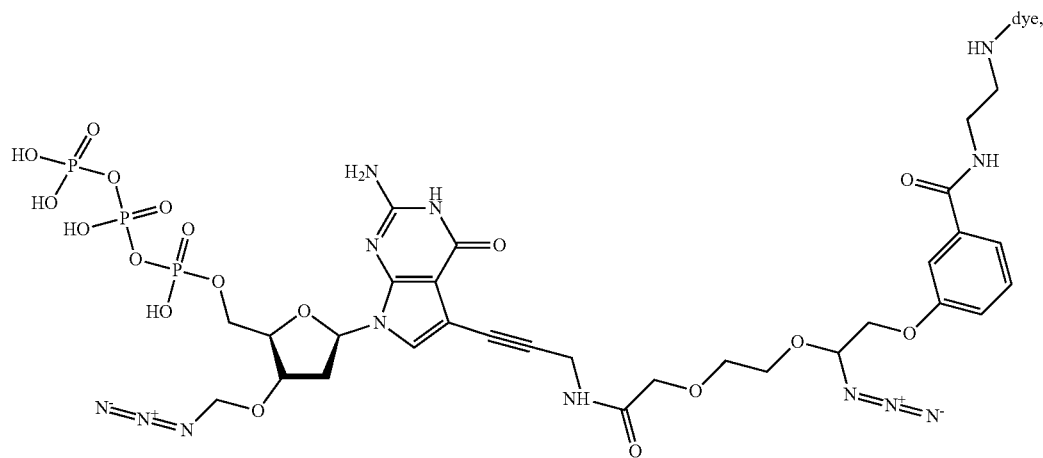
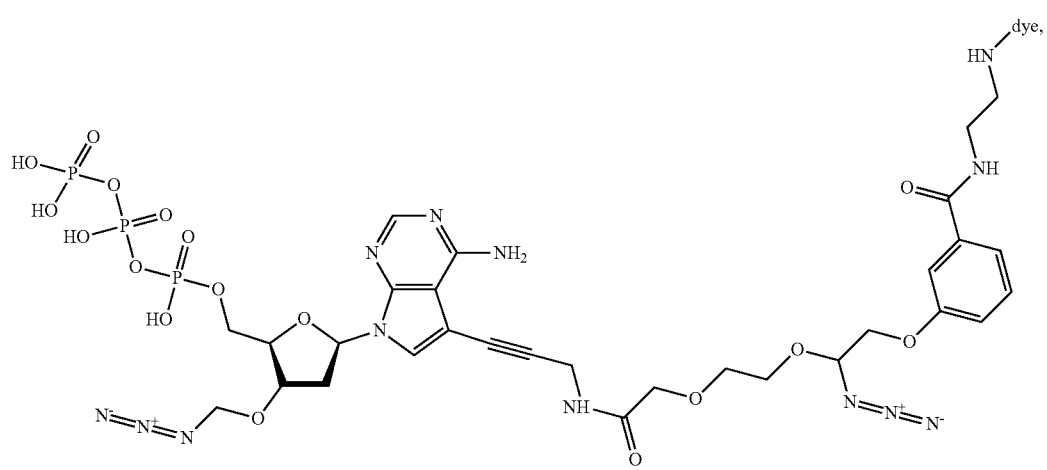
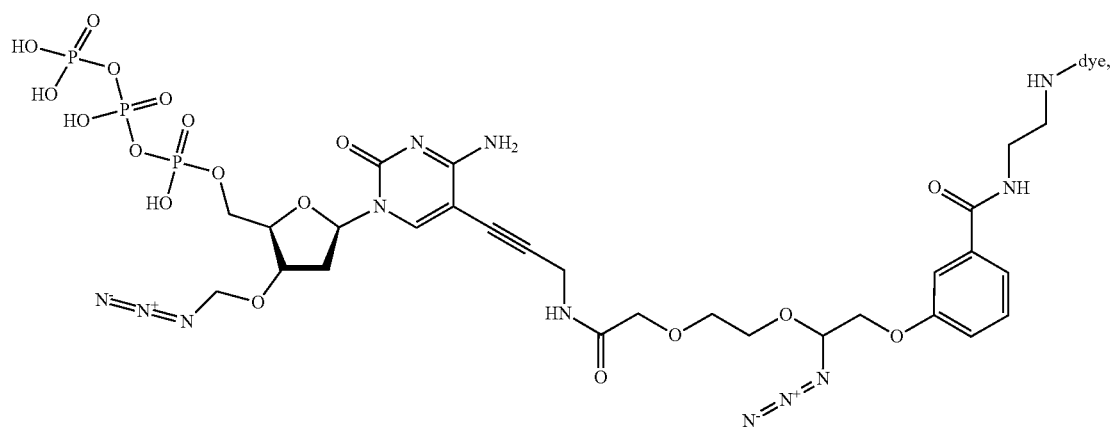

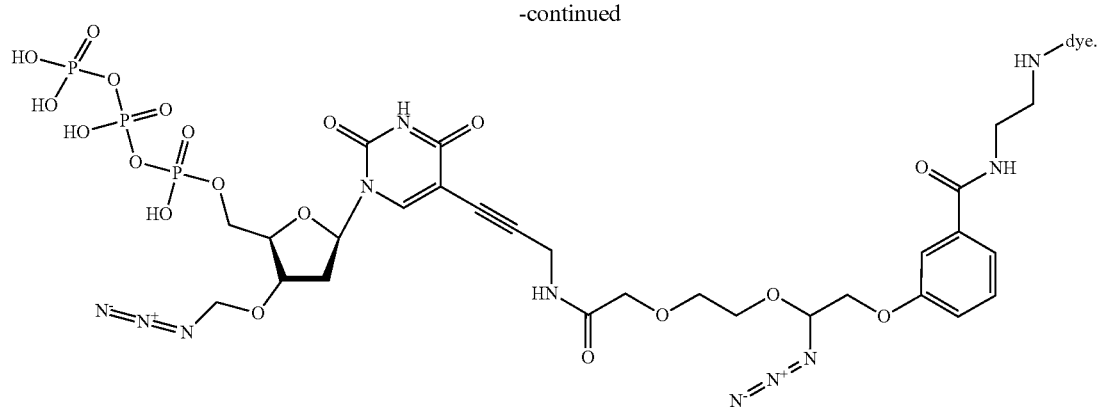

The experimental sample was the genomic DNA of *E. coli*, which was a standard sample carried by BGISEQ-500.

The azido-blocked nucleotide polymerization buffer contained 20 mM sodium chloride, 60 mM ammonium sulfate, 3 mM magnesium sulfate, 50 mM Tris, 5% DMSO, 0.05% Tween-20, and the reaction temperature was 55° C., 0.2 μM 9° N (the name of a DNA polymerase) DNA polymerase; pH was 9.0.

The excision reagent buffer contained 50 mM Tris-HCl, 1 M NaCl, 10 mM THPP; pH was 9.0.

2. Experimental Method

According to the manufacturer's instructions, a library for sequencing was prepared by extracting DNA from *E. coli* standard strain as raw material using MGIeasy™ DNA library preparation kit (Shenzhen Huada Zhizao Technology Co., Ltd.); referring to the BGISEQ-500 DNB preparation loading kit (Shenzhen Huada Zhizao Technology Co., Ltd., article number 85-05531-00), the prepared DNBs (DNA nanoballs) were loaded onto the sequencing chip of the BGISEQ-500 platform. The sequencing was performed using the BGISEQ-500 sequencing kit (SE50 V3.0, Shenzhen Huada Zhizao Technology Co., Ltd., article number PF-UM-PEV30). The specific sequencing steps were as follows:

Using the BGISEQ-500 platform, the same DNBs were loaded onto both sides of the chip, 4 cycles of sequencing was performed to the DNA random sequence on both sides, and the sequence at each position and its corresponding number were numbered, and then 100% formamide was used to elute the sequencing chain, and sequencing primer was reloaded; at one side the polymerization and excision of 3 cycles of fluorescently modified, reversibly blocked nucleotides (scar was left after excision) were performed, while at the other side, the polymerization and excision of 3 cycles of non-fluorescent, reversibly blocked nucleotides (there was no DNA at natural state after excision) were performed, and then at both sides, the polymerization of one cycle of fluorescently modified, reversibly blocked nucleotides was performed.

Figure 5:
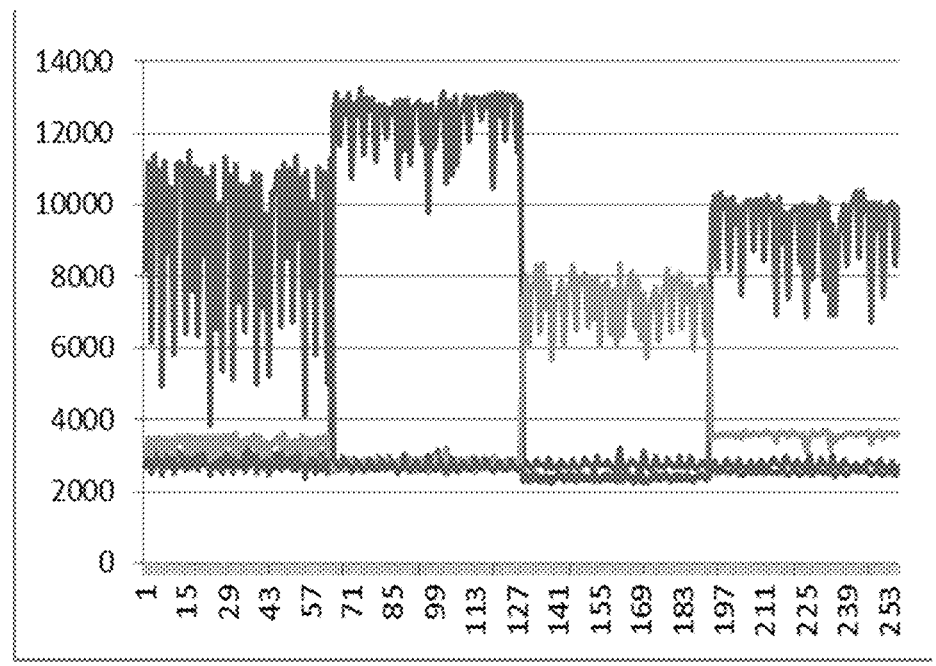
FIG. 5: The fluorescence signal value of the 4th base (4 types) after 64 NNN sequences carrying scar. Wherein: the ordinate represents the fluorescence signal value, the four groups of signal peak groups in the figure, from left to right, respectively represent the set of fluorescence signal values when the 4th base is A, C, G or T, and each group of signal peak groups contains 64 fluorescence signal values; the abscissa represents the permutation and combination of 64 NNN sequences when the 4th base is A, C, G, or T, there are a total of 64×4=256 permutations and combinations, of which 64 NNN sequences are shown in Table 2 as follows.
Figure 6:
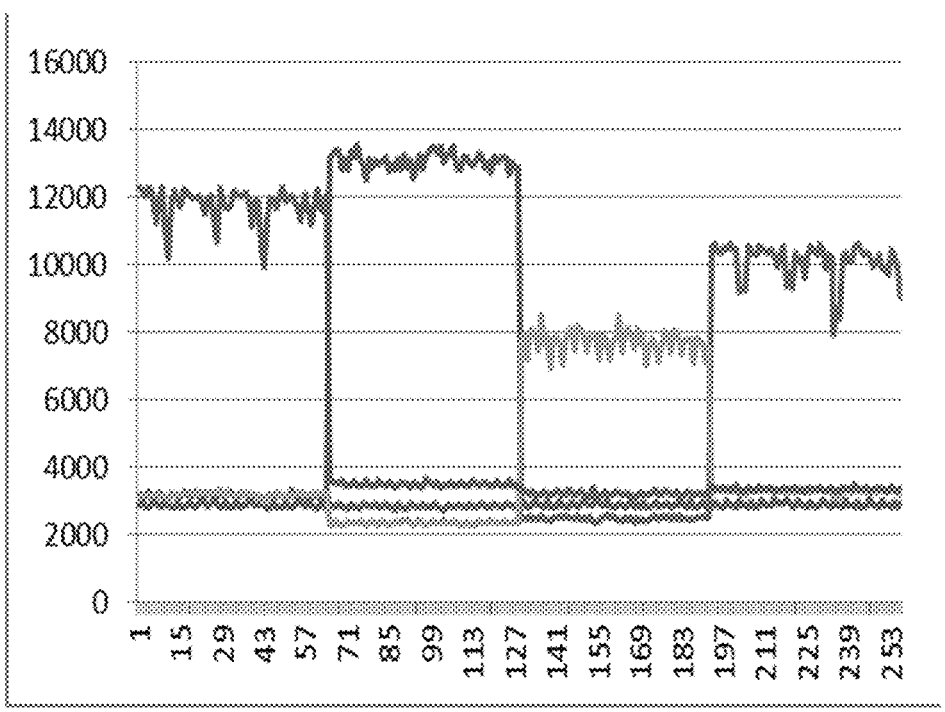
FIG. 6: The fluorescence signal value of the 4th base (4 types) after 64 NNN sequences without scar for the DNA in natural state. Wherein: the ordinate represents the fluorescence signal value, the four groups of signal peak groups in the figure, from left to right, respectively represent the set of fluorescence signal values when the 4th base is A, C, G or T, and each group of signal peak groups contains 64 fluorescence signal values; the abscissa represents the permutation and combination of 64 NNN sequences when the 4th base is A, C, G, or T, there are a total of 64×4=256 permutations and combinations, of which 64 NNN sequences are shown in Table 2 as follows.

Combining the sequence information of the previous 4 cycles, the distribution of the fluorescence signal of the 4th base after different NNN sequences was analyzed: FIG. 5 and FIG. 6 showed the signal effect of the scar atom modified bases on the next base, and the effect of natural nucleic acid pairs on the next base information, wherein the 64 permutations and combinations of NNN sequences were shown in Table 2 as below.

TABLE 2

64 permutations and combinations of 3 bases

| | |
|---|---|
| 1 | AAA |
| 2 | AAC |
| 3 | AAG |
| 4 | AAT |
| 5 | ACA |
| 6 | ACC |
| 7 | ACG |
| 8 | ACT |
| 9 | AGA |
| 10 | AGC |
| 11 | AGG |
| 12 | AGT |
| 13 | ATA |
| 14 | ATC |
| 15 | ATG |
| 16 | ATT |
| 17 | CAA |
| 18 | CAC |
| 19 | CAG |
| 20 | CAT |
| 21 | CCA |
| 22 | CCC |
| 23 | CCG |
| 24 | CCT |
| 25 | CGA |
| 26 | CGC |
| 27 | CGG |
| 28 | CGT |
| 29 | CTA |
| 30 | CTC |
| 31 | CTG |
| 32 | CTT |
| 33 | GAA |
| 34 | GAC |
| 35 | GAG |
| 36 | GAT |
| 37 | GCA |
| 38 | GCC |
| 39 | GCG |
| 40 | GCT |
| 41 | GGA |
| 42 | GGC |
| 43 | GGG |
| 44 | GGT |
| 45 | GTA |
| 46 | GTC |
| 47 | GTG |
| 48 | GTT |
| 49 | TAA |
| 50 | TAC |
| 51 | TAG |
| 52 | TAT |
| 53 | TCA |
| 54 | TCC |
| 55 | TCG |

TABLE 2-continued

| 64 permutations and combinations of 3 bases | |
|---|---|
| 56 | TCT |
| 57 | TGA |
| 58 | TGC |
| 59 | TGG |
| 60 | TGT |
| 61 | TTA |
| 62 | TTC |
| 63 | TTG |
| 64 | TTT |

The results showed that the DNA at natural state had little relationship with the previous NNN sequences, and there was no particularly strong fluctuation; however, the signals with scar had a very strong relationship with the NNN sequences, especially for the signals when the 4th base was A base, for example the first group of signal peak groups from the left as shown in FIG. 5 and the first group of signal peak groups from the left as shown in FIG. 6, some NNN sequences could cause the loss of about 70%.

The results also showed that the scar had an effect on the next base, especially when the 3' base in the NNN sequence was a G base, the scar made the next base signal very weak, so that the base recognition of the next base was prone to making mistake, especially when the A base was after G, it was more prone to making mistakes.

Although the specific embodiments of the present invention have been described in detail, those skilled in the art will understand that according to all the teachings that have been disclosed, various modifications and substitutions can be made to those details, and these changes are all within the protection scope of the present invention. The full scope of the present invention is given by the appended claims and any equivalents thereof.

What is claimed is:

1. A method for sequencing nucleic acid, comprising the following steps:
   (1) hybridizing a sequencing primer to a nucleic acid molecule to be tested;
   (2-1) ligating a nucleic acid probe to the sequencing primer;
   (3) detecting a detectable label being bound to the nucleic acid probe of the nucleic acid molecule to be tested, and obtaining information of a base to be tested;
   (4-1) ligating a dNTP having a blocking group ligated to the 3'-terminal thereof to a sequencing primer to which a nucleic acid probe is not ligated;
   (5) detecting a detectable label being bound to the nucleic acid probe of the nucleic acid molecule to be tested, and obtaining information of a base to be tested;
   (6-1) excising the blocking group ligated to the 3'-terminal of the dNTP;
   wherein,
   when the step (3) exists, the step (5) does not exist; or
   when the step (5) exists, the step (3) does not exist;
   wherein the nucleic acid probe comprises a first moiety, a second moiety, a linker and a detectable label, wherein:
   the first moiety has a sequencing base, which is one or more selected from the group consisting of A, T, U, C and G,
   the second moiety has random bases and/or universal bases, and the number of the bases is at least 3,
   the first moiety is ligated to the second moiety via the linker, and the ligation between the first moiety and the linker is cleavable, and
   the detectable label is ligated to the second moiety or the linker.

2. The method for sequencing nucleic acid according to claim 1, wherein between the step (2-1) and the step (3), the following step is further comprised:
   (2-2) eluting nucleic acid probes that are not ligated to the nucleic acid molecule to be tested.

3. The method for sequencing nucleic acid according to claim 1, wherein between the step (4-1) and the step (5), the following step is further comprised:
   (4-2) eluting dNTPs that are not ligated to the nucleic acid molecule to be tested.

4. The method for sequencing nucleic acid according to claim 1, wherein after the step (6-1), the following step is further comprised:
   (6-2) eluting a portion that is excised in the step (6-1).

5. The method for sequencing nucleic acid according to claim 1, wherein in the step (2-1), the time for the ligating is 0.5 to 30 minutes.

6. The method for sequencing nucleic acid according to claim 1, wherein in the step (2-1), the temperature for the ligating is an appropriate temperature at which the ligase being used works.

7. The method for sequencing nucleic acid according to claim 1,
   wherein:
   between the step (2-1) and the step (3), the following step is further comprised: (2-2) eluting nucleic acid probes that are not ligated to the nucleic acid molecule to be tested;
   between the step (4-1) and the step (5), the following step is further comprised: (4-2) eluting dNTPs that are not ligated to the nucleic acid molecule to be tested;
   after the step (6-1), the following step is further comprised: (6-2) eluting a portion that is excised in the step (6-1); and
   the eluting conditions of any two of the steps (2-2), (4-2) and (6-2) are the same, or the eluting conditions of the three steps are the same.

8. The method for sequencing nucleic acid according to claim 1, wherein in the step (4-1), the dNTP used has no detectable label.

9. The method for sequencing nucleic acid according to claim 1, wherein in the step (4-1), the dNTP is ligated by a polymerase-catalyzed polymerization reaction to the sequencing primer that is not ligated to the nucleic acid probe.

10. The method for sequencing nucleic acid according to claim 1, wherein in the step (6-1), conditions for excising the blocking group ligated to the 3'-terminal of the dNTP and the conditions for excising the remaining nucleotides on the nucleic acid probe that are not bound to the base to be tested are the same.

11. The method for sequencing nucleic acid according to claim 1, wherein the first moiety is located at the 5'-terminal or the 3'-terminal.

12. The method for sequencing nucleic acid according to claim 1, wherein the bases of the second moiety are 3 to 15 bases.

13. The method for sequencing nucleic acid according to claim 1, wherein the detectable label is a fluorophore; and the detectable label is ligated to the second moiety.

14. The method for sequencing nucleic acid according to claim 1, wherein the linker does not contain a sulfur atom.

15. The method for sequencing nucleic acid according to claim 1, wherein in the step (4-1), the blocking group is selected from the following Formula A to Formula D:

Formula A

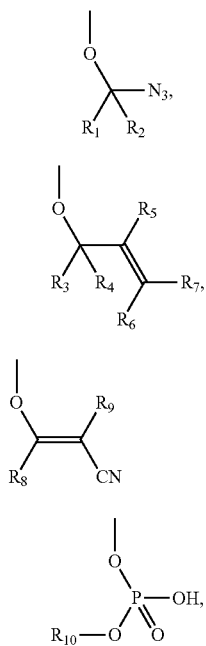

Formula B

Formula C and

Formula D wherein:
in Formula A, R₁ and R₂ are independently selected from the group consisting of H, F, CF₃, CHF₂, CH₂F, CH₂R alkane, COOR and CONHR, wherein R is independently $C_1$-$C_6$ alkyl;
in Formula B, R₃ to R₇ are independently selected from the group consisting of H and $C_1$-$C_6$ alkyl;
in formula C, R₈ and R₉ are independently selected from the group consisting of H, F, Cl, CF₃, nitro, cyano, $C_1$-$C_6$ alkoxy and $C_1$-$C_6$ carboxyl; and
in Formula D, R₁₀ is selected from $C_1$-$C_6$ alkyl.

16. A kit for use in the method for sequencing nucleic acid according to claim 1, comprising:
a nucleic acid probe, a ligase, a dNTP having a blocking group ligated to the 3'-terminal thereof, and a polymerase;
Reagent 1, which is used for excising the blocking group ligated to the 3'-terminal of dNTP;
Reagent 2, which is used for excising the remaining nucleotides on the nucleic acid probe that are not bound to the base to be tested;
wherein Reagent 1 and Reagent 2 are the same;
and wherein the kit further comprises an appropriate buffer for dissolving the nucleic acid probe;
Eluent 1 for eluting the nucleic acid probe, and Eluent 2 for eluting dNTP;
wherein
the nucleic acid probe comprises a first moiety, a second moiety, a linker and a detectable label, wherein:
the first moiety has a sequencing base, which is one or more selected from the group consisting of A, T, U, C and G,
the second moiety has random bases and/or universal bases, and the number of the bases is at least 3,
the first moiety is ligated to the second moiety via the linker, and the ligation between the first moiety and the linker is cleavable, and
the detectable label is ligated to the second moiety or to the linker.

17. The kit according to claim 16, wherein the first moiety is located at the 5'-terminal or the 3'-terminal.
18. The kit according to claim 16, wherein the bases of the second moiety are 3 to 15 bases.
19. The kit according to claim 16, wherein the detectable label is a fluorophore;
and the detectable label is ligated to the second moiety.
20. The kit according to claim 16, wherein the linker does not contain a sulfur atom; wherein the linker is selected from the group represented by the following Formula IV to Formula IX:

Formula IV

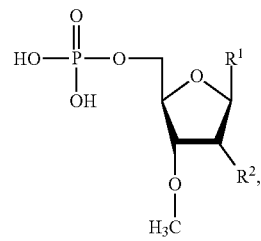

Formula V

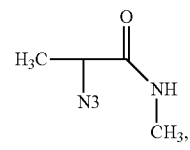

Formula VI

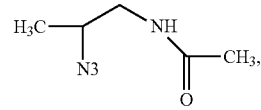

Formula VII

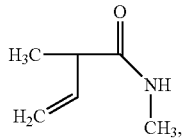

Formula VIII

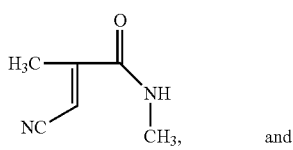

and

Formula IX

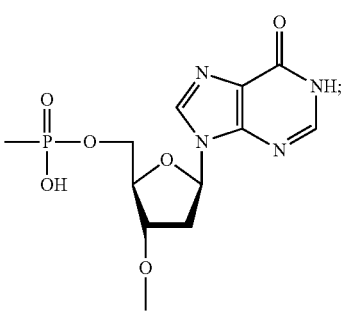

wherein, in Formula IV, R¹ is selected from the group consisting of H, OH, $C_1$-$C_6$ alkyl, $C_2$-$C_6$ alkenyl, and $C_2$-$C_6$ alkynyl; R² is selected from the group consisting of H, OH, F, Cl, and Br.
21. The kit according to claim 16, wherein the ligase is a DNA ligase, and the polymerase is a DNA polymerase.
22. The kit according to claim 21, which is characterized by any one or more of the following items 1) to 4):

1) The DNA ligase is one or more selected from the group consisting of T4 DNA ligase, T7 DNA ligase, and T3 DNA ligase;
2) The concentration of the nucleic acid probe is 0.1 μM to 5 μM;
3) The concentration of the DNA ligase is 0.01 μM to 2 μM; and
4) the reagents in the kit are free of silver ions.

23. The kit according to claim 16, wherein Reagent 1 or Reagent 2 is an endonuclease, an organic phosphine, or a complex of PdCl$_2$ and sulfonated triphenylphosphine.

24. The method for sequencing nucleic acid according to claim 1, wherein the above steps (2-1) to (5) are repeated, or the above steps (2-1) to (6-1) are repeated.

25. The method for sequencing nucleic acid according to claim 1, wherein in the step (6-1), further excising remaining nucleotides on the nucleic acid probe that are not bound to the base to be tested.

26. The method for sequencing nucleic acid according to claim 4, wherein the above steps (2-1) to (6-2) are repeated.

27. The method for sequencing nucleic acid according to claim 9, wherein the polymerization reaction is performed for a time of 0.5 to 10 minutes; at a temperature of 45° C. to 60° C.

28. The method for sequencing nucleic acid according to claim 13, wherein the detectable label is at least one selected from the group consisting of cy3, cy5, Texas Red, 6-FAMTM, AF532, AF647 and AF688.

29. The method for sequencing nucleic acid according to claim 1, wherein the linker is selected from the group represented by the following Formula IV to Formula IX:

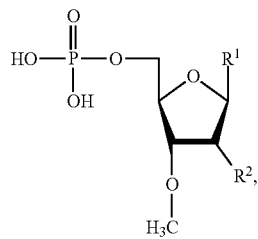

Formula IV

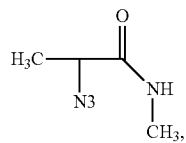

Formula V

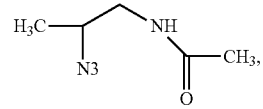

Formula VI

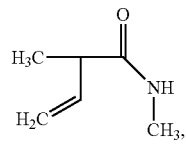

Formula VII

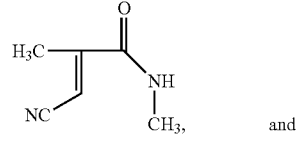

Formula VIII and

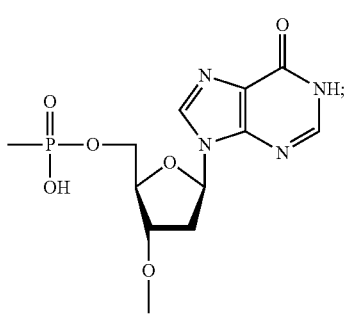

Formula IX wherein, in Formula IV, R$^1$ is selected from the group consisting of H, OH, C$_1$-C$_6$ alkyl, C$_2$-C$_6$ alkenyl, and C$_2$-C$_6$ alkynyl; R$^2$ is selected from the group consisting of H, OH, F, Cl, and Br.

* * * * *